United States Patent [19]

Samuels et al.

[11] Patent Number: 4,465,071
[45] Date of Patent: Aug. 14, 1984

[54] METHOD OF APPLYING SKIN CLIPS

[76] Inventors: Peter B. Samuels, 14708 Sutton St., Sherman Oaks, Calif. 91403; George S. Lee, 700 E. 9th St., Los Angeles, Calif. 90021

[21] Appl. No.: 421,121

[22] Filed: Sep. 22, 1982

Related U.S. Application Data

[60] Division of Ser. No. 314,533, Oct. 26, 1981, Pat. No. 4,399,810, which is a continuation of Ser. No. 98,128, Nov. 28, 1979, abandoned.

[51] Int. Cl.$^3$ .............................................. A61B 17/04
[52] U.S. Cl. .................................... 128/335; 128/337; 128/334 R; 227/DIG. 1
[58] Field of Search .................... 128/334 R, 335–337, 128/346; 227/DIG. 1 A–DIG. 1 C; 29/243.56

[56] References Cited

U.S. PATENT DOCUMENTS

| | | | |
|---|---|---|---|
| 3,047,874 | 8/1962 | Kelsey | 227/DIG. 1 |
| 3,068,870 | 12/1962 | Levin | 128/346 |
| 3,077,812 | 2/1963 | Dietrich | 85/49 |
| 3,098,232 | 7/1963 | Brown | 227/DIG. 1 |
| 3,487,836 | 1/1970 | Niebel | 128/346 |
| 3,604,425 | 9/1971 | Le Roy | 128/346 |
| 3,646,801 | 3/1972 | Caroli | 227/19 |
| 3,775,825 | 12/1973 | Wood | 227/DIG. 1 |
| 4,014,492 | 3/1977 | Rothfuss | 227/19 |
| 4,166,466 | 9/1979 | Jarvick | 227/19 X |
| 4,228,895 | 10/1980 | Larkin | 227/19 X |
| 4,399,810 | 8/1983 | Samuels et al. | 128/334 R |

FOREIGN PATENT DOCUMENTS

| | | | |
|---|---|---|---|
| 1094230 | 12/1960 | Fed. Rep. of Germany | 411/476 |
| 304673 | 9/1968 | Sweden | 85/49 |

OTHER PUBLICATIONS

Handout from Auto Suture Company

Primary Examiner—C. Fred Rosenbaum
Assistant Examiner—Gene B. Kartchner
Attorney, Agent, or Firm—McDougall, Hersh & Scott

[57] ABSTRACT

A spring clip and applier in which the skin clip is formed of a bail portion and consecutive outwardly and inwardly extending arm portions and the applier is formed with jaws mounted for movement in the direction towards and away from each other with recesses in the adjacent inner faces of the jaws dimensioned to receive a single clip therein and means for dispensing the foremost clip in a stack of clips from the applier into the recessed portions of the jaws.

2 Claims, 8 Drawing Figures

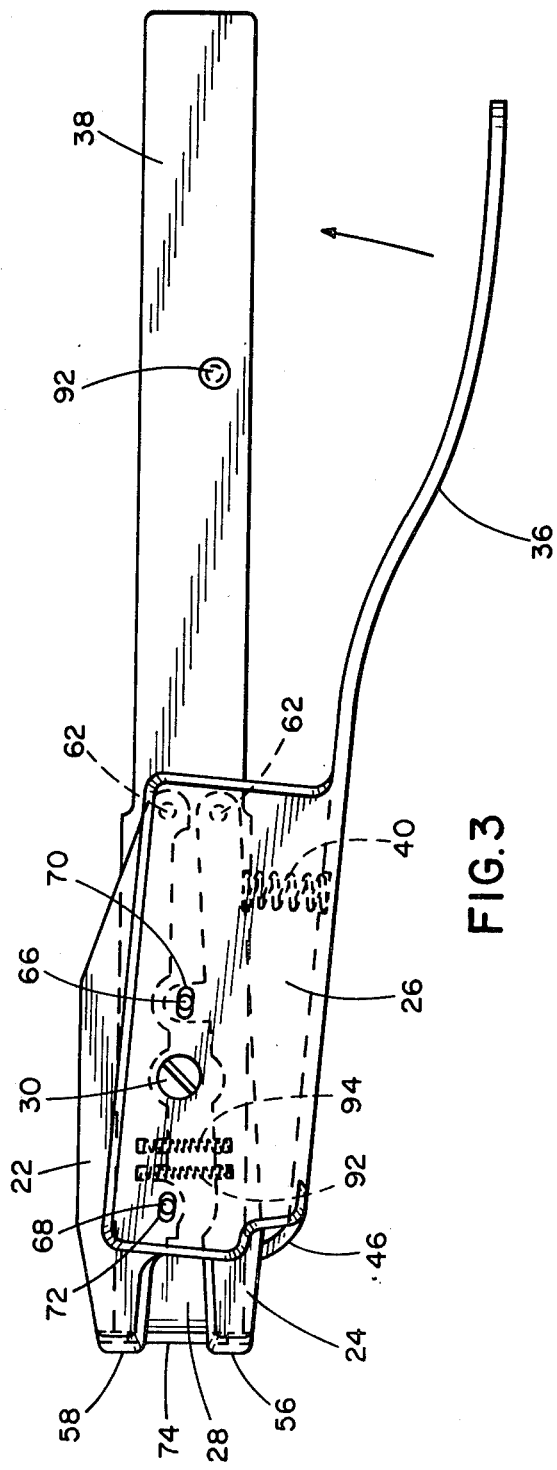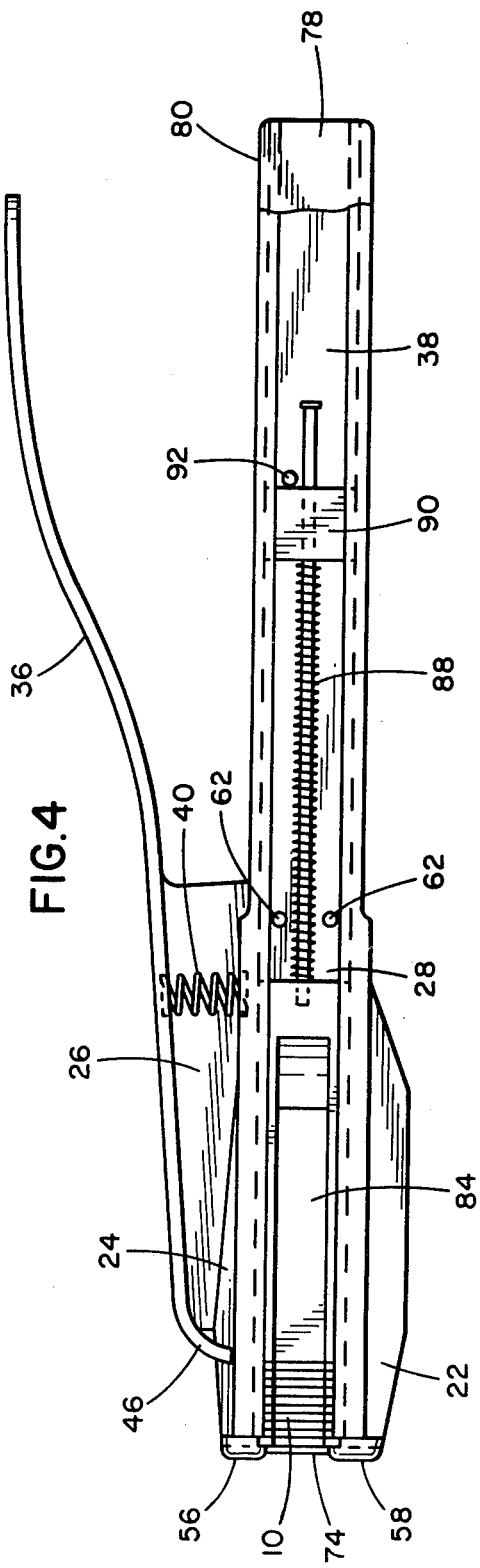

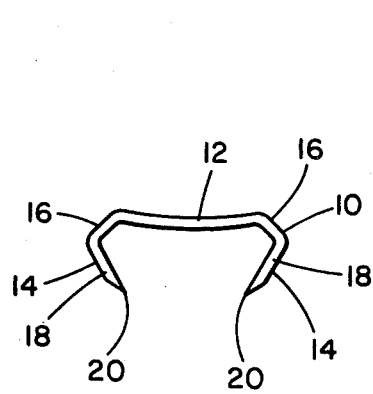
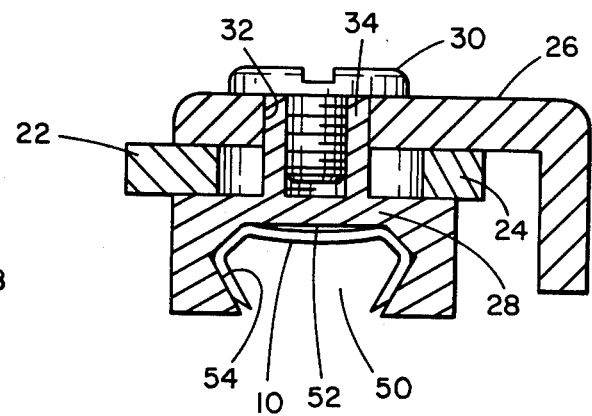
FIG. 5        FIG. 6
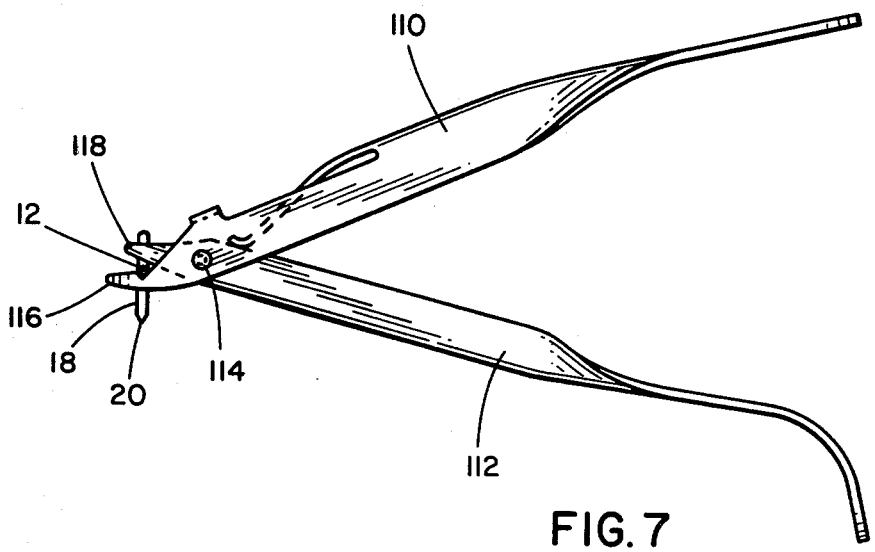
FIG. 7
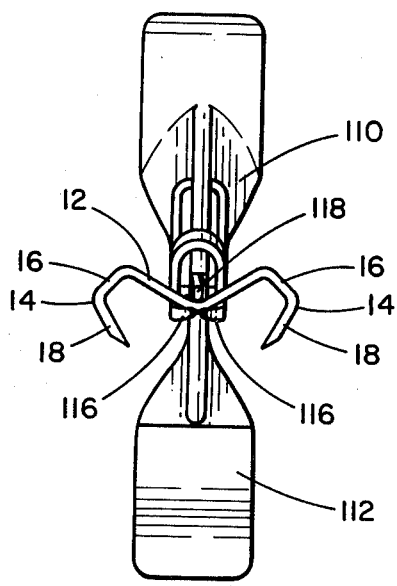
FIG. 8

METHOD OF APPLYING SKIN CLIPS

This is a division of application Ser. No. 314,533 filed Oct. 26, 1981, now U.S. Pat. No. 4,399,810 which, in turn, is a continuation of Ser. No. 98,128, filed Nov. 28, 1979, now abandoned.

FIELD OF INVENTION

This invention relates to a skin clip and applier for use in joinder of skin, as for closing wounds, incisions and the like.

BACKGROUND OF INVENTION

When lacerations and incisions of the skin layer occurs in wounds, surgical operations and the like, it has been the practice to stitch the separated portions of the skin together for the purpose of reducing scar formation and to accelerate healing. Such stiching operation constitutes a surgical operation wherein the separated sections of the skin are brought together and then stitched by needle and thread to hold the separated sections together until the wound has healed. When sufficient time has elapsed, such as three to six days, the stitches are removed by pulling the stitches from the wound after the thread has been severed.

Such stitching operation constitutes a painful procedure which lasts over a considerable period of time. In addition, it requires the services of both hands of one or more physicians to hold the separated sections of the skin together, thread the needle, pass the needle through the adjacent edge sections of the skin layer, tie the thread with the desired tension to close the wound, and then to sever the loose ends of the thread when the stitch has been completed, all of which takes considerable time coupled with the interference of the bleeding wound.

The art has turned more recently to the use of metal clips which are applied by clip applicators which operate more or less in the fashion of a stapler to clip the free edges of the skin in a manner to hold the edges together until the wound has healed. The use of clips in clip applicators has materially reduced the time required to close a wound and it has been effective to reduce the amount of effort and the amount of assistance required to effect skin closure.

In U.S. Pat. No. 733,723, U.S. Pat. No. 816,026, U.S. Pat. No. 3,273,562 and U.S. Pat. No. 3,775,825, description is made of surgical skin clips and clip applicators wherein preformed clips are individually applied by a suitable applicator for skin closure. Such prior devices have found little acceptance in the medical field for any number of reasons including cost, ease of application, ease of removal, and exposure while in position of use to inadvertent engagements, with resultant pain and/or disengagement of the clip.

OBJECTS OF THE INVENTION

It is an object of this invention to produce a new and improved skin clip which is capable of low cost manufacture of readily available materials; which is preformed to enable use in skin closure by engagement of the clip between actuating jaws; which reduces to a skin clip that engages the skin to a predetermined depth with little of the clip protruding above the skin, and in which the clip enables control as to the shape to which it is deformed for skin closure, and it is a related object to provide a new and improved applier for use with skin clips of the type described to effect closure of the clip for bringing the edges of the skin together, which is simple in construction and easy in operation, which can be formed of readily available and low cost materials to provide a throw away applier when the last of the clips have been dispensed therefrom, which is automatic in operation, and which is adapted to receive a multiplicity of clips to enable sequential application of the clips in rapid succession for wound closure, which allows for visualization of the area where the clip is applied to insure proper application of the clip, and which requires the use of only one hand thereby to relieve the surgeon in his operative procedures.

These and other objects and advantages of this invention will hereinafter appear and for purposes of illustration, but not of limitation, an embodiment of the invention is shown in the accompanying drawings in which:

FIG. 3 is a top plan view of the applier of FIG. 1;

FIG. 4 is a plan view of the applier of FIG. 1 taken from the bottom side;

FIG. 5 is an elevational view of the preformed clip embodying the features of this invention;

FIG. 6 is a sectional view taken partially along the line 6—6 of FIG. 1 showing the clip as received in the applier;

FIG. 7 is a perspective view illustrating a means for removal of the applied clip; and FIG. 8 is an elevational view showing the configuration of the clip removed by the means shown in FIG. 7.

DETAILED DESCRIPTION OF PREFERRED EMBODIMENT OF THE INVENTION

Figure 1:
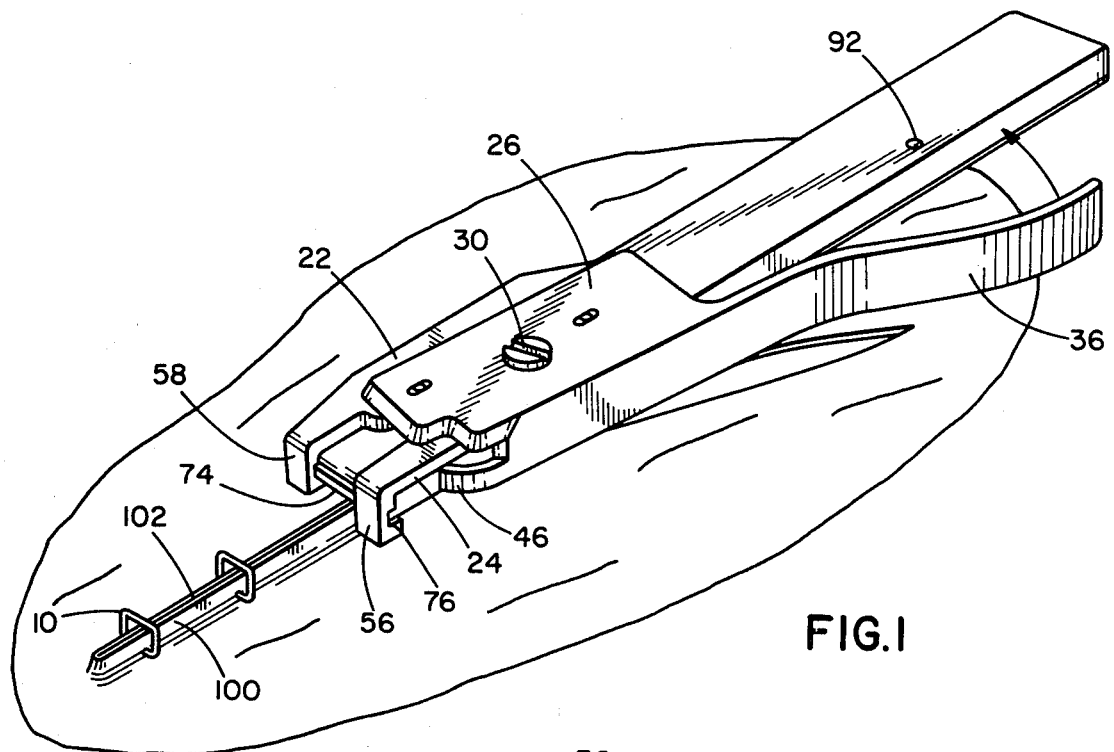
FIG. 1 is a perspective view of the clip applier embodying the features of this invention, showing the shape of the clip upon release from the applier.
Figure 2:
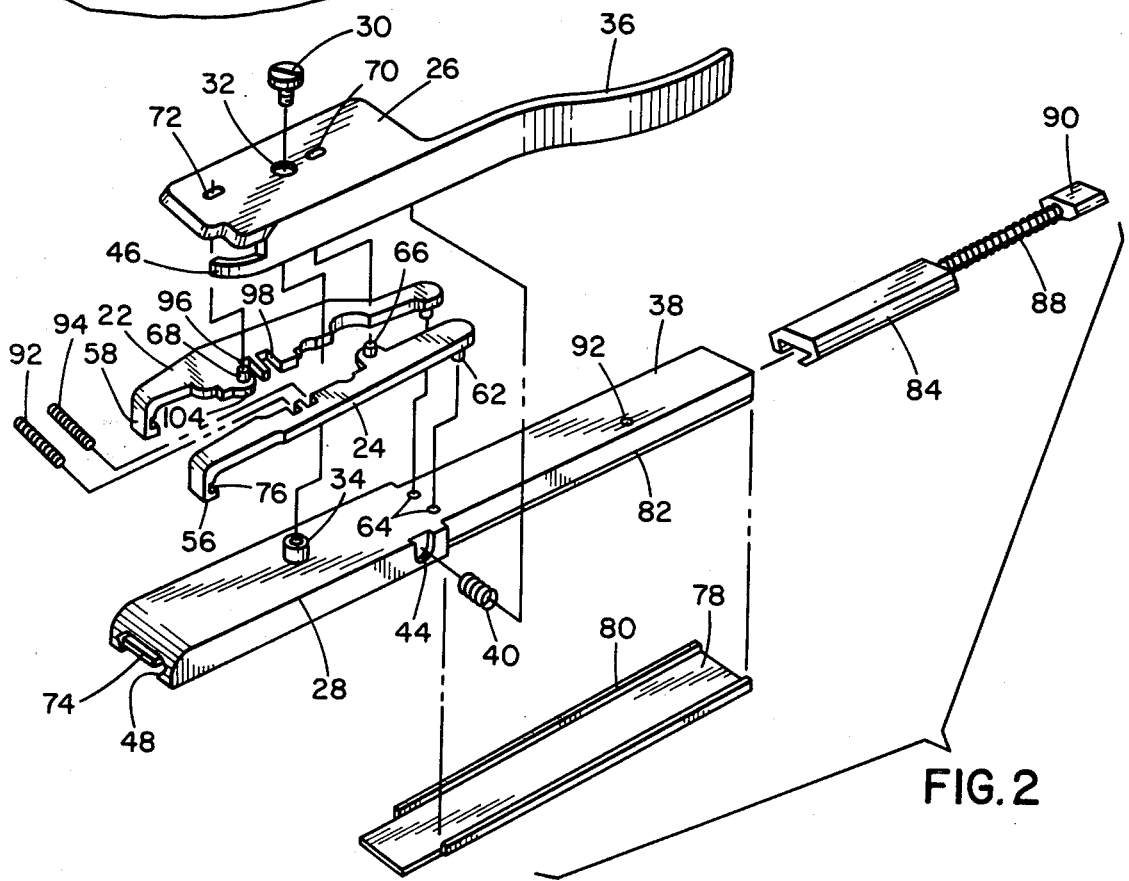
FIG. 2 is a perspective view of the elements making up the clip applier shown in their relative positions of assembly.

In the practice of this invention, use is made of a clip 10 formed of tantalum, titanium, stainless steel or the like deformable metal wire which retains the shape to which it is deformed. The clip is preformed to a U-shaped member having a bail portion 12 and arms 14 extending from the ends of the bail portion, with each arm being formed of an upper portion 16 and a lower free end portion 18 extending at about $90° \pm 10°$ from the upper portion 16 with the upper portion extending angularly outwardly at a contained angle of about $135° \pm 15°$ from the ends of the bail portion 12. The bail portion is preferably, though not necessarily, formed with a concave curvature for purposes which will hereinafter be described in applying the clip. The ends of the clip, which are spaced one from the other by an amount generally corresponding to the length of the bail portion, are reduced to a relatively sharp point 20 for piercing the skin.

Referring now to FIGS. 1–4 of the drawings, the applier comprises a pair of jaw plates 22 and 24 disposed between a top plate 26 and a bottom plate 28 with the top and bottom plates secured one to the other for relative rotational movement about a connecting screw bolt 30 or rivet which extends through an opening 32 in the top plate 26 for engagement with a threaded post 34 rigid with the bottom plate 28. The top plate has an integral handle portion 36 extending rearwardly thereof in spaced relation from the rearward extension 38 of the bottom plate 28. The handle portion is constantly urged in the direction away from the bottom plate to open position, as by means of a coil spring 40 disposed between the handle portion and the adjacent side wall of the bottom plate, with one end of the coil spring 40 anchored to the handle portion while the other end seats within a recess 44 provided in the side wall of the bottom plate, whereby the coil spring is retained therebetween. Means are provided to block movement of the handle portion beyond open position. In the illustrated modification, such blocking means comprises a curvilinear finger 46 extending inwardly from the forward end portion of the handle 36, forwardly of the pivot 30 and in crosswise alignment with the side wall of the bottom plate for engagement therewith when the handle portion is rocked about its pivot to open position.

The bottom side of the bottom plate 28 forms the top wall of an elongate enclosure 48 having a slot 50 extending therethrough and shaped to define a cross section corresponding generally to the cross section of the clip members whereby the enclosure is in the form of a cartridge in which a plurality (20-100) of clips 10 can be preloaded for use. In the illustrated modification, the slot is designed with a flat top wall 52 and facing V-shaped side walls 54 contoured to correspond with the contour of the side arms of the clips 10 and spaced one from the other by an amount for retaining the clips 10 in fitting relation therein.

The jaw plates 22 and 24 are formed with jaw members 56 and 58 which project downwardly from the forward ends thereof immediate adjacent the forward end of the bottom plate 28 and to a level of and preferably below the apex of the V-shaped side walls of the slot with the jaw members being spaced one from the other laterally by an amount less than the spaced relation between the apex portions forming the side walls of the slot and preferably by an amount corresponding to the spaced relation between the apex portions of the clip arms less the thickness of the clips in the side arm portions. The inner edge of each jaw member is formed with a recessed portion 60 having a width and depth corresponding to the thickness or cross section of a single clip so that the side walls of the recessed portions will be spaced one from the other by an amount corresponding to and preferably slightly in excess of the distance between the apices of the side arms of the clip so that only a single clip will be capable of being received in fitting relation within the crosswise aligned recessed portion of the jaw members.

The jaw members 56 and 58 are adapted to be displaced laterally in the direction towards and away from each other between closed and open position respectively in response to actuation of the handle 36 between closed and open positions, with a type of linear-rolling action as derived from remote pivots. As illustrated in the drawing, each of the jaw plates 22 and 24 is provided with a pivot pin 62 which depends from a rearward end portion of the plate into relative laterally spaced apart openings 64 in the bottom plate 28 to define the pivotal axes of the jaw plates 22 and 24. In order to provide for movement of the jaws 56 and 58 in opposite directions in response to actuation of the handle portion, one jaw plate 24 is pivotally connected to the top plate rearwardly of the connection between the top and bottom plates while the other is pivotally connected to the top plate forwardly of the pivot. Such pivotal connections are effected by pivot pins 66 and 68 extending forwardly from the jaw plates 24 and 22 into aligned openings 70 and 72 respectively in the top plate. The openings 70 and 72 are dimensioned to have a width corresponding to the width of the pivot pins 66 and 68 for transmission of movement of the top plate to the jaw plates, and the openings are dimensioned to have a length slightly greater than the cross section of the pivot pins to enable relative movement of the pivot pins in the openings to accommodate the relative movement therebetween during actuation of the top plate, by reason of the differences in the radii from their respective pivots.

The bottom plate 28 is provided with a relatively flat, horizontally disposed portion 74 which extends forwardly from the forward edge of the bottom plate for a distance corresponding to the thickness of a skin clip within the enclosure. Thus the extension projects beyond the inner surfaces of the jaw members 56 and 58 and, to enable lateral displacement of the jaw members in the direction towards and away from each other, the jaw members are each provided with a horizontally disposed slot 76 dimensioned to receive the extension therein for relative sliding movement.

A slide plate 78, having a width and length dimensioned to span the open bottom of the enclosure, is formed with side flanges 80 having an inturned upper edge for sliding engagement within slide grooves 82 in the outer side walls of the housing to enable the slide plate to be secured in sliding engagement with the bottom plate to seal the enclosure.

Means are provided constantly to urge the stack of clips within the enclosure toward the jaw members. For this purpose, there is provided a pusher block 84 contoured to correspond with the shape of the passage 50 through the housing and dimensioned slideably to be received therein. Means are provided constantly to urge the pusher block 84 in the direction towards the jaws for displacement of the stack of clips to push the foremost clip in the stack into the slotted portion between the jaw members 56 and 58. Such means for constantly urging the pusher block is illustrated in the drawing as a compression spring 88 confined between a rear plate 90 and the pusher block wherein the rear plate 90 is retained within a rearward portion of the enclosure as by means of a blocking nut 92.

To insure return of the jaw plates 22 and 24 to open position, means are provided constantly to urge the forward end portion of the jaw plates in a direction away from each other. Such means are illustrated as coil spring members 92 and 94 seated at their opposite ends in crosswise aligned slots 96 and 98 in the jaw plates.

In use, the cartridge housing 48 is filled with a column of clips. In normal position, the jaws 56 and 58 are spread by the coil cprings 92 and 94 to their open position.

Under these conditions, the pusher 84 has displaced the stack of clips 10 forwardly in the cartridge until the foremost clip in the stack is displaced into the recessed portion 60 between the jaws with the apices of the clip arms in the path of the jaw members with the bail 12 of the clip underlying the anvil-extension 74 from the bottom plate. Thus the foremost clip is retained in position of use between the jaws.

In applying the clip, the edges of the skin 100 are brought together with one hand and with the other hand, the applier is positioned in lengthwise alignment with the line 102 of skin separation with the jaws 56 and 58 on opposite sides of the line and at rest on the top surface of the skin 100. In response to squeezing of the handle 36 for displacement from open position to closed position, the jaw members 56 and 58 are displaced in the direction towards each other into engagement with the apex portions of the side walls of the clip members located therebetween. In response to actuation by the jaw members for displacement of the arms in the direction towards each other, the arms of the clip members are caused to bend about their ends of the bail portion as a fulcrum whereby the downwardly and inwardly extending end portions 18 of the clip are caused to move downwardly and inwardly along an arcuate path to engage the portion of the skin 100 immediately adjacent the edges to be joined, and to enter the skin layer to a predetermined depth whereby the skin portions are drawn together to establish an abutting relation. By the time that the jaw movement is completed, open movement to closed position, the clip 10 has been deformed into a substantially rectangular shape with the lower arm portions 18 embedded in the skin layer and extensions substantially horizontally while the upper arm portion 16 extends vertically therefrom firmly to clip the skin layers adjacent the wound. The overlying extension 74 serves as a backup which permits the bail portion 12 to straighten out during rotation of the arm portions about the ends of the bail as a fulcrum, thereby to facilitate deformation of the clip but only to the extent limited by the extension thereby to form the clip into a substantially rectangular section.

In the applied relation, the bail portion 12 is a short distance from the gripping end portion to project a calculated distance from the surface of the joined skin sections.

When the jaws are returned via the coil springs 92 and 94 to their initial spread or open position, the freed recessed portions return into alignment with the stack of clips in the cartridge whereby, upon clearance, the foremost clip in the stack is automatically displaced by the pusher 84 into the recessed portion between the jaw members readying the applier for immediate reuse. Thus the clip can be applied in a rapid sequence to close the wound in minimum time.

Because of the location of the jaws 56 and 58 at the forward end of the applier, and by reason of the openness at the jaw end portion, visibility is greatly increased for accurate and rapid position of the applier for correct insertion of the clip members.

The applier is intended to be discarded when the stack of clips has been used. However, it will be understood that instead of loading the clips directly into the applier, use can be made of a replaceable cartridge in whih clips are prepackaged for use in reloading the applier, in which vent the cartridge is in the form of the described housing adapted replaceably to be secured to the bottom plate in the position corresponding to the housing.

GENERAL DESCRIPTION

While it is preferred to make use of a clasp in which the upper and lower arm portions extend in angular relation as described, the desired results can be achieved when the arm portions have a configuration other than angular, such that the arms may constitute curvilinear sections in which the portion extending from the ends of the bail portion are inclined downwardly and outwardly from the ends thereof while the lower, pointed free end portion is inclined downwardly and inwardly at an angle whereby said end portion extends substantially horizontally or parallel to the bail portion when the clip is deformed to embed the end portion in the skin layer. One requirement in the construction of the clip is that a portion intermediate the ends of the arms extend outwardly beyond the remainder to define an apex portion engaged by the jaws for bending the arms about the ends of the bail portion as a fulcrum, during displacement of the jaws in the direction towards each other to closed position.

While it is preferred that the recessed portion 60 be dimensioned to have a depth corresponding to the thickness of a clip so as to accommodate only the foremost clip in the stack, the desired results can be achieved when the depth of the recessed portion 60 is less than the thickness of the clip but more than one-half the thickness of the clip so that the major portion of the clip member will be received in the recessed portion and lie in the path to be engaged by the jaws for bending of the arms during displacement of the jaws in the direction towards each other to closed position. The depth of the recessed portion should not exceed the thickness of the clip otherwise more than the outermost clip will lie in the path to be engaged by the jaws during movement to closed position.

The spaced relation between the jaws in open position is designed to be greater than the combined movement of the jaws between open and closed positions. Means are provided for limiting the movement of the jaws in the direction towards each other upon reaching closed position. In the illustrated modification, such means comprises abutments 104 in adjacent inner surfaces of the jaw plates. In the alternative, such means may comprise the dimensioning of the length of the slot 76 for engagement with the extension 74 when the jaw members have been displaced to closed position thereby to prevent movement beyond closed position.

While the force constantly urging the stack of clips forwardly in the direction of the jaws is ordinarily sufficient to retain the outermost clip in position of use within the recessed portion of the jaws, retention of the outermost clip in the recessed portion can be further benefited by inclining the lower side walls of the slots in an inwardly direction by an amount whereby the spaced relation therebetween, when the jaws are in open position, is less than the spaced relation between the outermost portions of the clip arms so as to militate against inadvertent dropping of the clip from between the jaws when displaced from the cartridge.

Removal of the clips can be easily and quickly effected as by a removing means such as a pair of lever arms 110 and 112 pivoted one on the other adjacent one end with the end portion of one arm beyond the pivot 114 being formed of laterally spaced prongs 116, while the end portion of the other arm is in the form of a single prong 118 which extends in vertical alignment with a midway portion between the spaced prongs 116. In use, the spaced prongs 116 are inserted into the space between the skin surface and the bail portion 12 of the clip 10 while the single prong 118 is positioned above the bail. In response to rotation about the pivot 114 to displace the single prong 118 into the area between the spaced prongs 116, an intermediate portion of the bail will be deformed into the area between the spaced prongs whereby the lateral portions of the bail will rotate about the single prong as a fulcrum to swing the clip arms outwardly and upwardly through an arc to withdraw the clip end portions from the skin. The withdrawn clip will have the configuration shown in FIG. 8.

It will be apparent that the clips can be applied one after the other in close sequence along the length of the wound as illustrated in FIG. 1 whereby the adjacent edges of the skin are held in abutting relation. It will also be apparent that substantially full visibility is available at the application zone so that the device can be accurately positioned for optimum utilization in the skin clipping operation. The depth of penetration of the pointed end portion of the clip arms is sufficient for engagement of the skin for displacement and for holding the skin in abutting relation but insufficient to pierce the skin to cause bleeding.

It will be understood that changes may be made in the details of construction, arrangement and operation without departing from the spirit of the invention, especially as defined in the following claims.

We claim:

1. A method of joining skin tissue together with reduced trauma comprising the steps of:
   (a) everting the skin tissue to be joined at the edges thereof;
   (b) placing over the tissue a skin clip which comprises a deformable wire-like member initially configured to include a bail portion and arms initially extending angularly downwardly and outwardly from the bail portion and finally downwardly and inwardly in an end portion remote from the bail portion, the ends of the arms being formed to piercing points over the everted tissue;
   (c) applying the clip to the tissue solely by lateral deformation of the clip;
   (d) repeating steps (b) and (c) at selected intervals along the length of the tissue to be joined;
   (e) releasing the skin tissue from the everted position to permit the edges thereof to move into abutting relation held in place by said clips.

2. The method of claim 1 wherein the steps of applying the clip involves lateral deformation only to the extent that the end portions of the clip describe an arc of less than 70 degrees during engagement and entry into the tissue thereby significantly limiting trauma thereto.

* * * * *